United States Patent [19]
van Acker et al.

[11] Patent Number: 6,093,845
[45] Date of Patent: Jul. 25, 2000

[54] ESTER CO-PRODUCTION

[75] Inventors: Patrick Eduard van Acker, Surrey, United Kingdom; Olivier Mathieu, Saint-Avold, France; Russell James Milner; Witold Franciszek Pacynko, both of East Yorkshire, United Kingdom

[73] Assignee: BP Chemicals Limited, London, United Kingdom

[21] Appl. No.: 09/200,233

[22] Filed: Nov. 25, 1998

Related U.S. Application Data

[63] Continuation of application No. PCT/GB98/00890, Mar. 24, 1998.

[30] Foreign Application Priority Data

Mar. 26, 1997 [GB] United Kingdom ................ 9706281

[51] Int. Cl.$^7$ .......................... C07C 67/08; C07C 67/54; B01D 3/13
[52] U.S. Cl. ........................ 560/239; 560/248; 203/14; 203/18; 203/19; 203/38; 203/98; 203/DIG. 19; 203/DIG. 34
[58] Field of Search ...................... 560/239, 248; 203/14, 18, 19, 34, 38, 98, DIG. 19

[56] References Cited

U.S. PATENT DOCUMENTS

| | | | |
|---|---|---|---|
| 3,692,822 | 9/1972 | Hay et al. | 260/475 R |
| 4,447,643 | 5/1984 | Feldman | 560/248 |
| 5,231,222 | 7/1993 | Papa et al. | 560/265 |

*Primary Examiner*—Shailendra Kumar
*Assistant Examiner*—Rosalynd Keys
*Attorney, Agent, or Firm*—Nixon & Vanderhye

[57] ABSTRACT

This invention relates to a process for the simultaneous co-production of ethyl acetate and n-butyl acetate. The process involves reacting a reaction mixture of ethanol, n-butanol and acetic acid in the liquid phase, in the presence of an acidic catalyst. The process is carried out in a series of reactor and distillation columns. The process is capable of using relatively impure reactants and provides for removing some of the aldehyde type impurities by the use of resin guard beds.

28 Claims, 1 Drawing Sheet

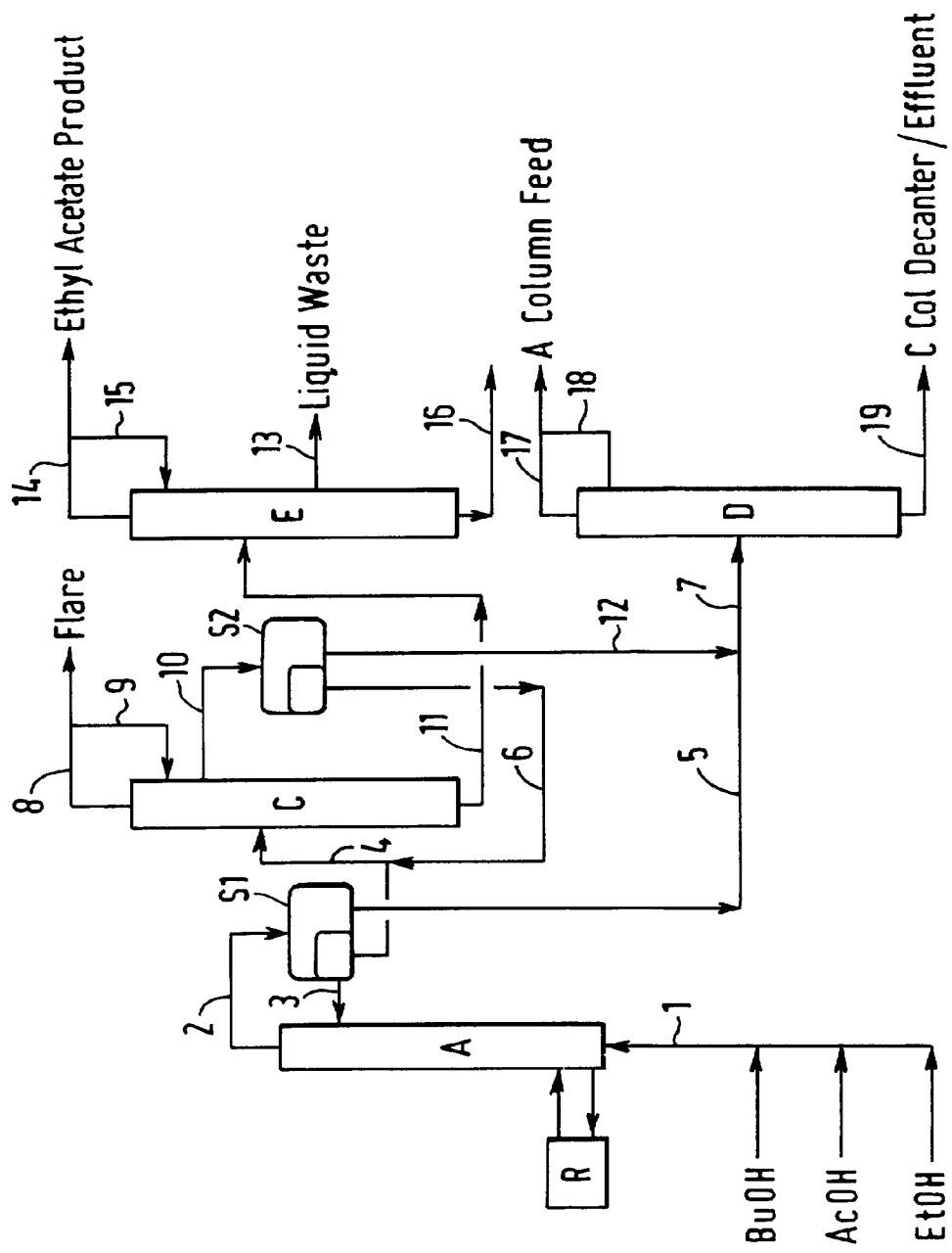

ESTER CO-PRODUCTION

This is a continuation of PCT application PCT/GB98/00890, filed Mar. 24, 1998.

The present invention relates to a process for the co-production of esters by reacting a mixture of alcohols with a carboxylic acid in the presence of a catalyst.

BACKGROUND OF THE INVENTION

It is well known to produce esters such as ethyl acetate or n-butyl acetate by reaction of ethanol or n-butanol respectively with acetic acid in the presence of an acidic catalyst. However, in the co-production of esters the formation of n-butyl acetate from n-butanol and acetic acid, difficulty is experienced in driving the reaction to completion thereby resulting in an n-butyl acetate product which is contaminated with n-butanol. It is also known to co-produce these esters in a single reactor by operating the reactor sequentially, ie by first producing one ester by reaction of the acid with the first alcohol and then in a swing operation changing over to the second alcohol to produce the second ester. In all of these reactions involving the use of a mixture of alcohols for esterification, it is important to use relatively pure reactants for reaction with acetic acid. This is particularly important if the esters are co-produced in a process for the simultaneous rather than the sequential production of both the esters. The use of reactants of high purity may not be economic commercially for it would significantly add to the cost of producing the esters. It has hitherto been relatively difficult to co-produce simultaneously a mixture of these esters from a relatively impure set of reactants. This is due to the following reasons. For instance, if the ethanol reactant is contaminated with impurities comprising carbonyl compounds such as eg crotonaldehyde, methyl ethyl ketone and the like, it is very difficult to separate the eventual ester product from the impurities. For instance, crotonaldehyde—whilst having a boiling point distinctly different from ethyl acetate—not only has an inordinately large impact on the odor of the ester product, even if present only in very small amounts, but also causes excessive fouling of the reaction column thereby resulting in a high boil-out frequency. On the other hand, methyl ethyl ketone has a boiling point which is very similar to that of ethyl acetate and separation of the two by eg distillation is impractical. Similarly, if the n-butanol reactant is contaminated by butyraldehyde—and this is usually the case if n-butanol is produced by the so called "oxo" process—the boiling point of butyraldehyde is very similar to ethyl acetate and hence cannot be readily separated.

SUMMARY OF THE INVENTION

It has now been found that such esters can be co-produced simultaneously from relatively impure feedstock by using a sequence of columns which enable the recovery of relatively pure esters from such a process.

Accordingly, the present invention is a process for the simultaneous co-production of ethyl acetate and n-butyl acetate, in a reaction of a mixture of ethanol and n-butanol with acetic acid in the liquid phase in the presence of an acidic catalyst characterized in that:

i. the reactants comprising ethanol, n-butanol and acetic acid is fed to the base of a reaction Column A which contains the acidic esterification catalyst and is maintained at elevated temperature to form a product comprising ethyl acetate and n-butyl acetate which rises up the Column A, ii. the overheads from Column A comprising the mixture of ethyl acetate and n-butyl acetate are fed, optionally after a decantation step, to about the upper half of a distillation Column C operated under elevated temperature whereby:
  a. a light ends fraction is separated from the reaction products and recovered as overheads therefrom,
  b. a stream comprising predominantly ethyl acetate and n-butyl acetate is withdrawn from the base thereof and fed to the upper half of a purification Column E,
  c. a side-stream comprising the reactant alcohols, water and some of the esters is withdrawn from the upper half of Column C fed to a decanter wherefrom, EtOH is washed out of the stream, following decantation, the oil phase is returned to the Column C feed and the water phase fed, to Column D, iii. the stream comprising a mixture of ethyl acetate and n-butyl acetate is fractionated in Column E so as to recover:
  a. substantially pure ethyl acetate overhead,
  b. substantially pure n-butyl acetate from the base of Column E and
  c. a liquid waste stream at a point intermediate between the withdrawal points for (iii) (a) and (iii) (b) above and comprising the unwanted impurities including the unwanted carbonyl compounds which stream is discharged, and iv. the side-stream comprising a mixture of the esters and alcohols fed to Column D is fractionated so as to remove a mixture comprising predominantly ethanol and n-butanol along with small amounts of water, ethyl acetate and n-butyl acetate overhead, and water from the base of Column D.

BRIEF DESCRIPTION OF THE DRAWING

The invention will now be described by way of illustration with reference to the accompanying FIGURE which is a schematic view of an apparatus suitable for carrying out an embodiment of the present process.

DETAIL DESCRIPTION OF THE INVENTION

In the following description, it is to be noted the reference to actual trays and theoretical trays in various columns, especially the A and E columns, is based on the calculation that the tray efficiency is 50%. However, it will be well known to those skilled in the art that tray efficiencies can be controlled or varied depending upon the other conditions prevalent or used in such columns and hence alternative numbers of actual trays and theoretical trays can be readily calculated and employed to achieve the same or similar results without detracting from the invention.

The esterification reaction in the process of the present invention occurs in the base of Column A which acts as a combination of a reaction vessel and a kettle (boiler), the kettle being located in the base of the column. It is preferred to recycle any residue from the base of this column back to the reaction vessel, especially if Column A is not an integrated reaction vessel and kettle. The amount of the acetic acid present in the kettle has to be controlled in order to minimize the passage of the acid overhead along with the reaction products thereby avoiding contamination of the n-butyl acetate product with the reactant acid. This has to be balanced by the need to control the rate of the reaction, ie the higher the acidity in the kettle, the faster the rate of reaction. The amount of acetic acid in the base of Column A is suitably in the range from 30 to 75% of the total kettle contents. The actual amount of acetic acid will depend on the ratio of ethyl acetate: butyl acetate to be produced and therefore the respective weight of the reactant alcohols added to the feed. Thus, in order to produce a product comprising a mixture of ethyl acetate (70%) and n-butyl acetate (30%), it is believed that the acidity in the kettle based on the acetic acid reactant and the acid catalyst is suitably about 53% by weight. Due to the presence of butyraldehyde and n-butanol in the reaction mixture, in addition to n-butyl acetate, ethanol and ethyl acetate in Column A, this Column has a temperature profile which enables these unwanted impurities to be separated, recovered and recycled as appropriate. For instance, depending upon the temperature profile of this Column A, this Column may either be provided with a side-draw (to remove impurities and waste) or such a side-draw may be omitted and the impurities removed from Column E along with the liquid waste stream removed therefrom. Column A is suitably operated at a temperature profile ranging from 105° C. at the base of the Column to 80° C. at the top of the Column at atmospheric pressure. Column A may be a packed or unpacked column. Column A suitably has 25 to 70 actual (12–35 theoretical) plates at 2 barg pressure, preferably from 45 to 60 actual (24–30 theoretical) plates and is suitably operated at a reflux ratio in the range of 0.5:1 to 4:1, eg 0.5:1. Within this range, however, if internal condensation is taken into account, the reflux ratios may be effectively 1.5:1.

The overheads from Column A are suitably fed through a decanter S1 to carry out a preliminary separation of an aqueous phase comprising predominantly water, the reactant alcohols and small amount of the product esters, from an oily phase which comprises predominantly the product esters with relatively small amounts of water and the reactant alcohols and other impurities. The aqueous phase from the decanter is suitably fed directly to Column D either separately or admixed with the water used to wash the side-stream from Column C. In some cases the water may also be returned back to the column as an aqueous reflux particularly if high butyl acetate:ethyl acetate (greater than 30:70) ratios are being manufactured. The oily phase recovered from S1 is fed to Column C but a portion of this oily phase may be recycled to the upper half of Column A.

Column C is a purification column and is suitably operated at a temperature profile ranging from 115° C. at the base of the Column to 85° C. at the top of the Column at 2 barg pressure. Column C may be a packed column and is packed with Mellapack® packing (supplied by Sulzer). Column C suitably has 20 to 60 theoretical plates, preferably from 35 to 45 theoretical plates and is suitably operated under total reflux at 2 barg pressure with a small purge taken off overhead to maintain the temperature at the top of the Column constant. The amount taken off would depend upon the nature of the impurities present in the purge. As with the overheads from Column A, the side-stream from Column C can be mixed with water and fed to a decanter S2 to separate an aqueous phase which is similar in composition to the aqueous phase recovered from the decanter S1 associated with Column A and comprises water, the reactant alcohols, small amounts of the product esters and trace impurities. The oily phase from the decanter S2 associated with Column C also comprises mixture of the product esters, some of the reactant alcohols and a small amount of water. This oily phase can be recycled to Column C either separately or admixed with the oily phase from decanter S1.

Decanters S1 and S2 are suitably operated at or below the temperature at which the relevant streams are fed to said decanters.

Column E is suitably a distillation column and suitably contains 20 to 60 theoretical plates, preferably from 23 to 40 theoretical plates, typically 28 plates (which corresponds to about 55 actual trays at a tray efficiency of about 0.5 per theoretical plate). Column E is fed from the product recovered from the base of Column C and comprises predominantly ethyl acetate (60–70%) and n-butyl acetate (40–30%), but also contains small amounts of other impurities. These range from ethanol (10 ppm), n-butanol (about 5000–6000 ppm) aldehydes and ketones (600–1000 ppm), other esters (1500–2000 ppm). The feed to Column E is suitably pre-heated to a temperature of about 60–80° C., eg 70° C. and is fed to about tray 15 (theoretical plate 8) if it has 55 trays (28 theoretical plates). A waste stream comprising crotonaldehyde, unreacted n-butanol, ethyl propionate, butyl formate, isomers of methyl pentanone and small amounts of methyl ethyl ketone and butyraldehyde is withdrawn from a side take-off point suitably located in the vapour space above tray 35 (theoretical plate 18) of a 55 tray (28 theoretical plates) column. Column E is suitably operated at a reflux ratio in the range from 1:1 to 4:1, eg 2:1. Within this range, however, if internal condensation is taken into account, the reflux ratio may be effectively 3:1. The temperature profile of this Column E at atmospheric pressure typically ranges from:

| Plates 1–15 = | 77–100° C. |
|---|---|
| Plates 15–24 = | 81–125° C. |
| Plates 24–33 = | 125–130° C. |

The ethyl acetate and butyl acetate recovered from Column E are of a very high quality in spite of containing some trace impurities. For instance, ethyl acetate may contain trace amounts of methyl ethyl ketone and butyraidehyde due to the very close proximity of the boiling points of these compounds. n-Butyl acetate has a purity greater than 99.5% which is fully acceptable for most commercial purposes but may contain trace amounts of n-butanol, methyl pentanones, isomers of n-butyl acetate and some dibutyl ether.

Column D is a simple distillation column where the overheads comprising mainly of the reactant alcohols, water and product ester azeotropes. These are recycled as feed to Column A and base products comprising water and small amounts of organics may either be recycled to the decanter S2 associated with Column C or can be discharged as effluent.

The process of the present invention may be further refined by use of resin guard beds to remove last traces of any aldehydes such as eg crotonaldehyde or butyraldehyde in the desired ester products. Butyraldehyde, for instance, is an impurity always associated with n-butanol and can be removed either before n-butanol is used as the reactant or can be removed from the ester products. The resin for this purpose is suitably macro-reticular resin and is preferably a salt such as eg a halide of a trimethyl ammonium substituent on one of the aromatic groups of a styrene-divinylbenzene polymer backbone or it is an acrylate resin. The resins are suitably used in the form of highly porous beads which have a high surface area. Prior to use, it is preferable to wash the resin with an acid such as hydrochloric acid at moderately elevated temperature such as eg 50° C. so as to form a salt with any free amines present which can then be readily washed away from the system. Thereafter, the acid washed resin is suitably treated with a solution comprising bisulphite using eg a 1 molar sodium bisulphite solution. This solution is suitably eluted through a bed of the chosen acid-washed resin at a flow rate typically of about 2 bed volumes (hereafter BV) per hour. Approximately 100 ml of bisulphite solution may have to be used for each 10 ml of resin volume at room temperature. During this step the chloride ions are exchanged for bisulphite ions. Once the resin is charged with the desired ions, it is washed several times with de-aerated water until the water conductivity of the eluate emerging from the resin is at a minimum (typically better than 100 microsiemens). This final conductivity is dependent on how well the wash water has been degassed since bisulphite reacts with oxygen to form sulphites and sulphates. The latter ions are divalent and take up two sites on the resin thus causing a bisulphite ion to be lost from the resin and thereby diminishing the effectiveness of the resin. The water-washed resin is then conditioned with a solvent such as eg ethanol to ensure that the carbonyl impurities, the n-butanol and the esters in the product have optimum access to the bisulphite sites on the resin. This conditioning process removes the water from the resin but may cause some shrinkage of the resin and discoloration of the eluate. The resin so conditioned may be further conditioned by passing the solvent to be treated through the bed and this may result in further shrinkage of the resin. The displaced conditioning solvent such as eg ethanol along with any other solvents in the reaction product can be recycled back to be re-processed. These pretreatment steps are required because carbonyl compounds tend to undergo an addition reaction with bisulphite thereby retaining the bisulphite-carbonyl addition complex on the resin to which it becomes attached.

In order for the resin to work efficiently, especially when removing butyraldehyde from n-butanol, the butyraldehyde present in the solvent, eg n-butanol or ethyl acetate, requires certain amount of time to access the bisulphite sites located in the pores of the resin. This may determine the minimum residence time which in turn is dependent upon the viscosity of the conditioning solvent and the amount of shrinkage of the resin observed. With n-butanol it has been observed that very high residence times are required unless water is added which probably acts to reduce the shrinkage of the resin and the viscosity of the conditioning solvent. For a commercially viable process it is possible to visualize the addition of up to 10% by weight water to the n-butanol so as to improve the efficiency of the resin and thus reduce the residence time required to eg 40 to 60 minutes (1.0–1.5 BV/hour). Under these conditions from 90–95% of the butyraldehyde can be removed.

In the presence of an acid catalyst, an alcohol can react with an aldehyde to form acetals. Solutions of sodium bisulphite in water are slightly acidic. It is therefore possible that this reaction may also occur on the surface of the resin giving rise to the formation of 1,1-dibutoxy butane (an acetal) if the impurities being treated are butyraldehyde and n-butanol. This reaction should be avoided because it is reversible under the esterification reaction conditions and may release free butyraldehyde thereby adversely affecting the efficiency of the resin bed. It has been found that the formation of the acetal can be monitored in the eluate from the resin bed and the acetal is only eluted once the resin bed became full. Since acetal formation requires the presence of a proton, this may have been due to the formation of sulphite from the bisulphite in situ in the resin bed. This can occur due to the ingress of oxygen into the system at some stage or due to the abstraction of a proton from the bisulphite. It is therefore important to exercise care to ensure that all water and solvents used during the treatment of the resin and the subsequent purification of the ester products or the alcohols are de-aerated.

Similarly, butyraldehyde can be removed from ethyl acetate by passing the contaminated ethyl acetate through the treated resin. This method allows the amount of butyraldehyde from levels of 70 ppm to below limits of detection.

As an alternative to the process of forming a bisulphite-aldehyde complex described above, it would be possible to dose one or more of the feedstock such as eg ethanol or n-butanol with bisuiphite and pass the dosed solution through an ion-exchange resin before it is fed to Column A. This method would mitigate the problems of progressive deactivation of the resin bed described above.

It is possible to regenerate the bisulphite treated resin bed after use. It has been found that the aldehyde-bisulphite addition complex is dependent upon pH and temperature. Therefore, it is possible to regenerate the used bed containing the complex by subjecting said bed to higher pH's and temperatures in order to promote the breakdown of the complex. The pH can be controlled by using weak bases such as sodium bicarbonate solution (pH 10–11) or by using organic amines such as eg triethylamine which can also be used as an aqueous solution. The choice of amine would be determined by its ability to be separated from the butyraldehyde and recovered for the purposes of re-use. This may be done by refluxing the mixture of the aldehyde and the amine in a suitable solvent which would enable butyraldehyde to undergo an aldol type condensation and thus form a higher molecular weight product. This will facilitate the separation of the amine therefrom and the separation would be improved further if the amine is relatively volatile so that it can be recovered overhead from a batch still where the recovery is processed. In the alternative, if an amine such as triethanolamnine is used, this would enable butyraldehyde to be removed overhead from the batch still leaving behind an aqueous solution of triethanol amine from which the amine can be recovered and re-used later. The butyraldehye can be sent to the plant flare system.

As a further alternative to the process of forming a bisulphite-aldehyde complex described above, it would be possible to dose one or more of the feedstock such as eg ethanol or n-butanol with a solution comprising a metal borohydride such as eg sodium borohydride and pass the dosed solution through an ion-exchange resin before it is fed to Column A. In this method, it may be necessary to dilute the alcohol such as eg butanol to a 90% w/w solution and then to this solution is added a solution of sodium borohydride in the presence of sodium hydroxide (eg 12% w/w sodium borohydride solution in 14 M NaOH) whereupon any aldehyde present is converted to the corresponding alcohol, eg butyraldehyde to butanol. The rate of addition of the borohydride solution to the aqueous alcoholic solution is eg about 0.14 g per kg of the aqueous alcoholic solution which corresponds to the amount of borohydride required to convert about 70 ppm of butyraldehyde. It is believed that 1 mole of sodium borohydride is capable of reducing 2.4 moles of butyraidehyde. The resultant mixture predominating in an alcohol/water mixture is allowed to react for a period of between 30 and 60 minutes and passed through one or more beds of a resin representing a combination of anionic and cationic resins such as eg UP252 (cation resin in the hydrogen form) and UP900 (anion resin the hydroxide form) which are both based on a styrene divinyl benzene copolymer matrix (ultra-pure resins, both ex Rohm & Haas) to remove the borate and sodium ions from the mixture. The resin beds avoid the build-up of undesirable inorganic materials in the reactor. This method is particularly important for removal of butyraldehyde from butanol and hence the n-butanol feed to the reactor is suitably fed through these resin beds before entering the reaction Column A.

At high levels of sodium borohydride addition (such as when butyraldehyde levels are close to 70 ppm) some of the salts eg sodium borates and sodium hydroxide fall out of solution as the solubility in 10 wt % water in butanol is exceeded. For this reason it is necessary to protect the resin beds by introducing a filter into the system ahead of the resin beds. In this way fouling of the resin beds can be prevented. Both the borohydride reaction and the ion exchange process within the resin bed can be operated at a variety of temperatures but higher temperatures are favoured but may be more costly for the process overall. Temperatures of 30° C. where found to give acceptable performance.

If resins other than the ultrapure UP252 and UP900 resins are used then some preconditioning of the resin may be required in order to remove polymer fragments remaining from the resin manufacturing process which would otherwise unnecessarily pass into the reaction column. The preconditioning involves washing the resin with water and then with the butanol/water mixture to be used as solvent. In addition, if resins other than the ultrapure UP252 and UP900 resins are used then some further preconditioning of the resin may be required depending upon the form in which the resins are supplied. For example, if the cation resin is supplied in the sodium form then this needs to be converted to the hydrogen form prior to use. Similarly if the anion resin is supplied in the chloride form then this needs to be converted to the hydroxide form. This preconditioning process is similar to the regeneration process described below and is performed twice before using the resin.

The used resins can be regenerated for re-use as follows: The resin bed for anion exchange is regenerated by subjecting the used bed to a sequential treatment with water, 1M NaOH solution, water and a butanol/water mixture respectively. The resin bed for cation exchange is regenerated by subjecting the used bed to a sequential treatment with water, 1M sulphuric acid, water and a butanol/water mixture respectively.

The accompanying drawing represents a schematic flow diagram of the present process in which all percentages and ppm quoted are—unless otherwise stated—by weight. In the description below, the data for Columns A and E were obtained from laboratory scale experiments whereas those for Columns C and D were obtained from Aspen simulations and existing plant data. The drawing shows the co-production of ethyl acetate and n-butyl acetate without the resin treatment for removal of carbonyl compounds. For this process, ethanol (EtOH), acetic acid (AcOH) and n-butanol (BuOH) are fed through line (1) into Column A. The fresh ethanol feed typically contained between 89.0 and 90.5% of ethanol, between 7 and 10% water, <0.3% acetaldehyde, <2.0% diethylether, <0.1% methyl ethyl ketone, <0.05% crotonaldehyde and <0.25% non volatile residues, and had a density of about 815 kg/m$^3$ at 15° C. The fresh acetic acid feed had 99.85% acetic acid, <0.15% water, <0.05% of each of formic acid and acetaldehyde, and 100 ppm of propionic acid. The fresh n-butanol feed had a purity of >99.7%, and had <0.05% water, <1500 ppm of isobutanol, <1000 ppm of di-n-butyl ether and <0.05% carbonyls as n-butanal, <0.05% sec-butanol and had a density of 0.809–0.810 kg/l at 20° C. The relative proportions of the fresh initial feeds to Column A was: ethanol (31.3%), n-butanol (15.6%), acetic acid (51.5%) and incidental water (1.6%). Column A, a 5 cm (2 inch) Oldershaw column, has 45 trays (corresponding to 23 theoretical plates) and is provided with a recycle system (R) at the base thereof where the kettle is located. The temperature profile of this column operating at atmospheric pressure and a reflux ratio of 0.5:1 (1.5:1 when internal reflux included), was as follows:

| | |
|---|---|
| Top tray = | 81° C. |
| Tray 15 = | 85° C. |
| Tray 25 = | 87° C. |
| Tray 33 = | 93° C. |
| Tray 45 = | 103° C. |

The overheads from Column A were cooled to between 60 and 40° C. and fed via line (2) into a decanter (S1) to enable the separation of the oil phase predominating in organic compounds from the aqueous phase predominating in water and water soluble components. After allowing a short duration to enable phase separation, part of the oil phase from decanter (S1) was recycled via line (3) to the top of Column A as reflux, at a reflux ratio of 0.5:1 and the remainder of the oil phase was fed to Column C via line (4), the latter including a recycle stream from decanter (S2). The aqueous phase from decanter (S1) was fed via line (5) into Column D which had 10 actual plates above the feed point and 24 actual plates below the feed point.

Column C is a primarily a purification column its function is to separate the light end impurities from the desired products as well as enabling recovery of any alcohols remaining in the decanter (S1) oil phase. Column C has 15.4 meters of packing (Mellapack® packing, ex Sulzer) having a height equivalent to a theoretical plate of about 0.4 m. This corresponds to 38–39 theoretical plates. The feed to Column C is primarily the oily phase from decanter (S1) which is supplemented with the oily phase from decanter (S2) associated with Column C and is described below. The feed to this Column C is fed at a point such that the column had 11 meters of packing below the feed point and 4.4 meters of packing above the feed point. This Column C has the following temperature profile when operating at a pressure of 2 barg:

| | |
|---|---|
| Base of Column C | 119° C. |
| At 9.9 meters from the Top of Column | 116° C. |
| At 2.2 meters from the Top of Column | 100° C. |
| At the Top of the Column | 85° C. |

This column is operated almost at total reflux with a small amount of impurities being continuously purged from the system. A side stream (10) is withdrawn from Column C at a point in the column where alcohols such as ethanol are most concentrated. This side stream take-off, which is located just above the feed point (10) was fed, after water washing (not shown) into decanter (S2) where it was allowed to separate into aqueous and oily phases as previously with decanter (S1). The oily phase was recycled via line (6) to be admixed with the oily phase (line (4)) from decanter (S1) and fed to the Column C via line (4). The aqueous phase from decanter (S2) was withdrawn via line (12) to be admixed with the XXaqueous phase (line (5)) from decanter (S1) and fed to Column D via line (7). The base product from Column C which comprised predominantly of the desired esters, ethyl acetate and n-butyl acetate was withdrawn via line (11) and fed to a separation Column E. The heads product which comprised mainly of light ends was removed via line (8) and was mostly flared off with a portion being returned to the top of the column via line (9).

Column E was a 5 cm (2 inch) Oldershaw column having 55 actual trays (corresponding to 28 theoretical plates) and the feed to this column from the base of Column C was via line (11). The feed to this Column E had the following composition: ethyl acetate (67.83%), n-butyl acetate (31.35%) and the remainder were by-products and other impurities of which principally the combined amounts of (i) n-butanol and isopropyl acetate—5835 ppm, (ii) formate esters—800 ppm, (iii) other acetate esters—1025 ppm and (iv) ketones—710 ppm; the amounts of butyraldehyde and methyl ethyl ketone in this feed was not analysed. This feed was pre-heated to a temperature of 70° C. and fed to tray 15 of Column E as stated above. This column had the following temperature profile:

| | |
|---|---|
| Base tray (55) = | 127.5° C. |
| Tray 50 = | 126.7° C. |
| Tray 45 = | 126° C. |
| Tray 40 = | 125° C. |
| Tray 38 = | 123° C. |
| Tray 35 = | 120° C. (liquid waste stream withdrawal) |
| Tray 30 = | 93° C. |
| Tray 25 = | 81.3° C. |
| Tray 20 = | 80.6° C. |
| Tray 15 = | 81° C. |
| Tray 5 = | 79° C., and |
| Tray 1 (Top) = | 77° C. |

A liquid waste stream (13) was continuously taken-off in the vapour space above tray 35 of this column at the rate of about 10.5 g/hr at 120° C. This column was operated under atmospheric pressure at a feed rate of 690 g/hr, a reflux ratio of 2:1 (3:1 when internal reflux is taken into account) and the liquid waste stream (13) withdrawn represented 1.5% of the feed rate. The point of the liquid waste stream withdrawal was optimised to maximise the removal of the major impurities such as crotonaldehyde, unreacted n-butanol, ethyl propionate, butyl formate and isomers of methyl pentanone. Only small quantities of methyl ethyl ketone and butyraldehyde were removed in this column. The compositional data for the heads product (line (14)), base product (line (16)) and the liquid waste stream (line (13)) withdrawn from Column E after 50 hours of continuous operation under the above conditions was as follows:

HEADS PRODUCT Column E

| Component | Concentration |
|---|---|
| Ethanol | <10 ppm |
| Ethyl Acetate | 99.99% |
| Ethyl propionate | <10 ppm |
| Crotonaldehyde | <10 ppm |
| n-Butanol + iso-propyl acetate | 20 ppm |

BASE PRODUCT Column E

| Component | Concentration |
|---|---|
| Ethanol | <5 ppm |
| Ethyl Acetate | <5 ppm |
| n-Butanol & isopropyl acetate | 290 ppm |
| Acetic acid | <50 ppm |
| Butyl formate | 25 ppm |
| Methyl pentanones | 825 ppm |
| sec- and iso-butyl acetates | 1085 ppm |
| n-Butyl acetate | 99.7% |
| n-Pentyl acetate | 100 ppm |

BASE PRODUCT Column E—continued

| Component | Concentration |
|---|---|
| Di-butyl ether | 105 ppm |
| $C_7H_{14}O_2$ Ester | 390 ppm |
| $C_8H_{10}O$ Ketone | 35 ppm |

WASTE LIQUID STREAM Column E

| Component | Concentration |
|---|---|
| Ethanol | <5 ppm |
| Ethyl Acetate | 5.3% |
| Crotonaldehyde | 0.46% |
| Ethylpropionate + iso-butyl formate | 2.50% |
| Methyl pentanones | 2.57% |
| sec- and iso-butyl acetates | 3.10% |
| n-Butyl acetate | 53.9% |
| Butyl formate | 1.35% |
| n-Butanol + iso-propyl acetate | 30.4% |

The aqueous phases from the decanters (S1 and S2) associated with Columns A and C are fed via line (7) to Column D. This column D simply separates water from any dissolved organic materials. Column D has 34 actual trays and the aqueous phases from lines (5) and (12) are fed via line (7) into Column D at tray 10. Column D is operated at a reflux ratio of 1.5:1 and temperature profile of 125 to 93° C. at a pressure of 1.2 barg as follows:

| | |
|---|---|
| Top tray = | 93° C. |
| Tray 4 = | 96° C. |
| Tray 6 = | 97° C. |
| Tray 14 = | 117° C. |
| Tray 34 (Base) = | 125° C. |

The overheads from Column D are recovered via line (17) and returned (not shown) to the feed line (1) to Column A. A portion of this overhead from Column D is returned via line (18) as recycle/reflux to Column D. The base products from Column D are removed via line (19) and comprise mainly water which is returned (not shown) either to decanter (S2) of Column C along with line (10) or is discharged as an effluent.

We claim:

1. A process for the simultaneous co-production of ethyl acetate and n-butyl acetate, in a reaction of a mixture of ethanol and n-butanol with acetic acid in the liquid phase in the presence of an acidic catalyst, said process comprising the steps of:
   i. feeding the reactants comprising ethanol, n-butanol and acetic acid to the base of a reaction Column A which contains the acidic esterification catalyst and maintaining the reactants at elevated temperature to form a product comprising ethyl acetate and n-butyl acetate which rises up the Column A,
   ii. feeding the overheads from Column A comprising the mixture of ethyl acetate and n-butyl acetate, optionally after a decantation step, to about the upper half of a distillation Column C operated under elevated temperature whereby:
      a. a light ends fraction is separated from the reaction products and recovered as overheads therefrom, b. a stream comprising predominantly ethyl acetate and n-butyl acetate is withdrawn from the base thereof and fed to the upper half of a purification Column E, c. a side-stream comprising the reactant alcohols, water and some of the esters is withdrawn from the upper half of Column C fed to a decanter wherefrom, following decantation, the oil phase is returned to the Column C feed and the aqueous phase fed to Column D, iii. fractionating the stream comprising a mixture of ethyl acetate and n-butyl acetate in Column E so as to recover:

a. substantially pure ethyl acetate overhead, b. substantially pure n-butyl acetate from the base of Column E and c. a liquid waste stream at a point intermediate between the withdrawal points for (iii) (a) and (iii) (b) above and comprising the unwanted impurities including the unwanted carbonyl compounds which stream is discharged, and iv. fractionating the side-stream comprising a mixture of the esters and alcohols fed to Column D so as to remove a mixture comprising predominantly ethanol and n-butanol along with small amounts of water, ethyl acetate and n-butyl acetate overhead, and water from the base of Column D.

2. A process according to claim 1 wherein the esterification reaction occurs in the base of Column A which acts as a combination of a reaction vessel and a kettle (boiler), the kettle being located in the base of the column.

3. A process according to claim 1 wherein Column A is an integrated reaction vessel and kettle and the amount of the acetic acid present in the kettle is controlled in order to minimized the passage of the acid overhead along with the reaction products thereby avoiding contamination of the n-butyl acetate product with the reactant acid.

4. A process according to claim 1 wherein the amount of acetic acid in the base of Column A is in the range from 30 to 75% based on the total weight of the reactor contents used in the esterification reaction in Column A.

5. A process according to claim 4 wherein the acidity in the kettle based on the acetic acid reactant and the acid catalyst is about 53% by weight for making 30:70 weight ratio of butyl acetate: ethyl acetate.

6. A process according to claim 1 wherein Column A is operated at a temperature profile ranging from 105° C. at the base of the Column to 80° C. at the top of the Column at atmospheric pressure.

7. A process according to claim 1 wherein Column A has 25 to 60 actual (12–30 theoretical) plates at 2 barg pressure and is operated at a reflux ratio in the range of 0.5:1 to 4:1.

8. A process according to claim 1 wherein the overheads from Column A are fed through a decanter S1 to carry out a preliminary separation of an aqueous phase comprising predominantly water, the reactant alcohols and small amount of the product esters, from an oily phase which comprises predominantly the product esters with relatively small amounts of water and the reactant alcohols and other impurities.

9. A process according to claim 8 wherein the bulk of the oily phase recovered from S1 is fed to Column C with a small portion of this oily phase being recycled to the upper half of Column A.

10. A process according to claim 1 wherein Column C is operated at a temperature profile ranging from 119° C. at the base of the Column to 85° C. at the top of the Column at 2 barg pressure.

11. A process according to claim 1 wherein Column C is a packed column.

12. A process according to claim 1 wherein Column C has 20 to 60 theoretical plates and is operated under total reflux at 2 barg pressure.

13. A process according to claim 1 wherein the side-stream from Column C is is mixed with water and fed to a decanter S2 to separate an aqueous phase from an oily phase.

14. A process according to claim 13 wherein the oily phase from the decanter S2 associated with Column C also comprises mixture of the product esters, some of the reactant alcohols and a small amount of water and is recycled to Column C either separately or admixed with the oily phase from decanter S1.

15. A process according to claim 1 wherein Column E is a distillation column and contains 20 to 60 theoretical plates.

16. A process according to claim 1 wherein Column E is fed from the product recovered from the base of Column C and comprises predominantly ethyl acetate (60–70%) and n-butyl acetate (40–30%) and small amounts of other impurities ranging from ethanol (10 ppm), n-butanol (about 5000–6000 ppm) aldehydes and ketones (600–1000 ppm), and other esters (1500–2000 ppm).

17. A process according to claim 1 wherein the feed to Column E is pre-heated to a temperature of about 60–80° C. and is operated at a reflux ratio in the range from 1:1 to 4:1.

18. A process according to claim 1 wherein Column E has a temperature profile at atmospheric pressure ranging from 80–130° C.

19. A process according to claim 1 wherein Column D is a distillation column where the overheads comprise mainly of the reactant alcohols, water and product ester azeotropes.

20. A process according to claim 1 wherein one or more of the feedstock and/or process streams are treated with resin guard beds capable of retaining aldehydes therein to remove last traces of any aldehydes therefrom.

21. A process according to claim 20 wherein the resin guard bed comprises a macro-reticular resin.

22. A process according to claim 20 wherein the resin guard bed comprises an amino substituted styrene-divinyl benzene polymer backbone or is an acrylic resin.

23. A process according to claim 22 wherein the resin guard bed comprises a salt of a trimethyl ammonium substituent on one of the aromatic groups of a styrene-divinylbenzene polymer backbone.

24. A process according to claim 23 wherein the salt is a halide salt.

25. A process according to claim 20 wherein the resins in the guard bed are used in the form of highly porous beads which have a high surface area.

26. A process according to claim 22 wherein, prior to use, the resin is charged with bisulphite ions which are capable of forming a bisulphite-carbonyl addition complex which is retained on the resin.

27. A process according to claim 22 wherein one or more of the feedstock selected from ethanol and n-butanol is dosed with a solution comprising bisulphite ions and the dosed solution is passed through resin guard bed before it is fed to Column A.

28. A process according to claim 22 wherein one or more of the feedstock selected from ethanol and n-butanol is dosed with a solution comprising a metal borohydride and an alkali and the dosed solution is passed through at least one resin guard bed before it is fed to Column A.

* * * * *